(12) United States Patent
Snorrason, I

(10) Patent No.: US 9,730,919 B2
(45) Date of Patent: Aug. 15, 2017

(54) METHOD OF TREATING SKIN DISEASES

(71) Applicant: Ernir Snorrason, I, Mos (IS)

(72) Inventor: Ernir Snorrason, I, Mos (IS)

(73) Assignee: Hakon Hakonarson, Malvern, PA (US)

( * ) Notice: Subject to any disclaimer, the term of this patent is extended or adjusted under 35 U.S.C. 154(b) by 0 days.

(21) Appl. No.: 14/737,998

(22) Filed: Jun. 12, 2015

(65) Prior Publication Data

US 2015/0297574 A1 Oct. 22, 2015

Related U.S. Application Data

(62) Division of application No. 11/665,280, filed as application No. PCT/IB2005/003508 on Oct. 12, 2005, now Pat. No. 9,186,345.

(30) Foreign Application Priority Data

Oct. 12, 2004 (GB) .................................. 0422634.6
Mar. 1, 2005 (GB) .................................. 0504202.3

(51) Int. Cl.
*A61K 31/445* (2006.01)
*A61K 9/00* (2006.01)
*A61K 31/00* (2006.01)
*A61K 31/55* (2006.01)

(52) U.S. Cl.
CPC .......... *A61K 31/445* (2013.01); *A61K 9/0014* (2013.01); *A61K 31/00* (2013.01); *A61K 31/55* (2013.01)

(58) Field of Classification Search
CPC ........................... A61K 31/445; A61K 9/0014
See application file for complete search history.

(56) References Cited

FOREIGN PATENT DOCUMENTS

| EP | 0296560 A2 * | 12/1988 | ........... C07D 207/09 |
| WO | WO 9800119 A2 * | 1/1998 | ............. A61K 31/46 |
| WO | WO 9908672 A1 * | 2/1999 | ............. A61K 31/00 |

OTHER PUBLICATIONS

CAS Registry No. 120014-06-4 (Apr. 7, 1989).*
Merriam-Webster.com. 2014. http://merriam-webster.com/dictionary/wound (accessed Jun. 11, 2014).*
ARICEPT® ODT (Donepezil Hydrochloride Tablets): Prescribing Information. NDA 20-690/S-026 (Oct. 13, 2006).*
Lebwohl, Mark, and Suad Ali. "Treatment of psoriasis. Part 1. Topical therapy and phototherapy." Journal of the American Academy of Dermatology 45.4 (2001): 487-502.*
PubChem, Open Chemistry Database; Donepezil—C24H29NO3; Pub Chem CID:3152; https://pubchem.ncbi.nim.nih.gov/compound/donepezil, (accessed May 17, 2017).
Drugs.com, Aricept Side Effects, Generic Name: donepezil; https://www.drugs.com/sfx/aricept-side-effects.html,(accessed May 17, 2017).

* cited by examiner

*Primary Examiner* — Bethany Barham
*Assistant Examiner* — Peter Anthopolos
(74) *Attorney, Agent, or Firm* — Thomas Kim

(57) ABSTRACT

Acetylcholinesterase inhibitors, such as galantamine or donepezil, have been to be useful in the topical treatment of skin diseases and skin problems.

12 Claims, 1 Drawing Sheet

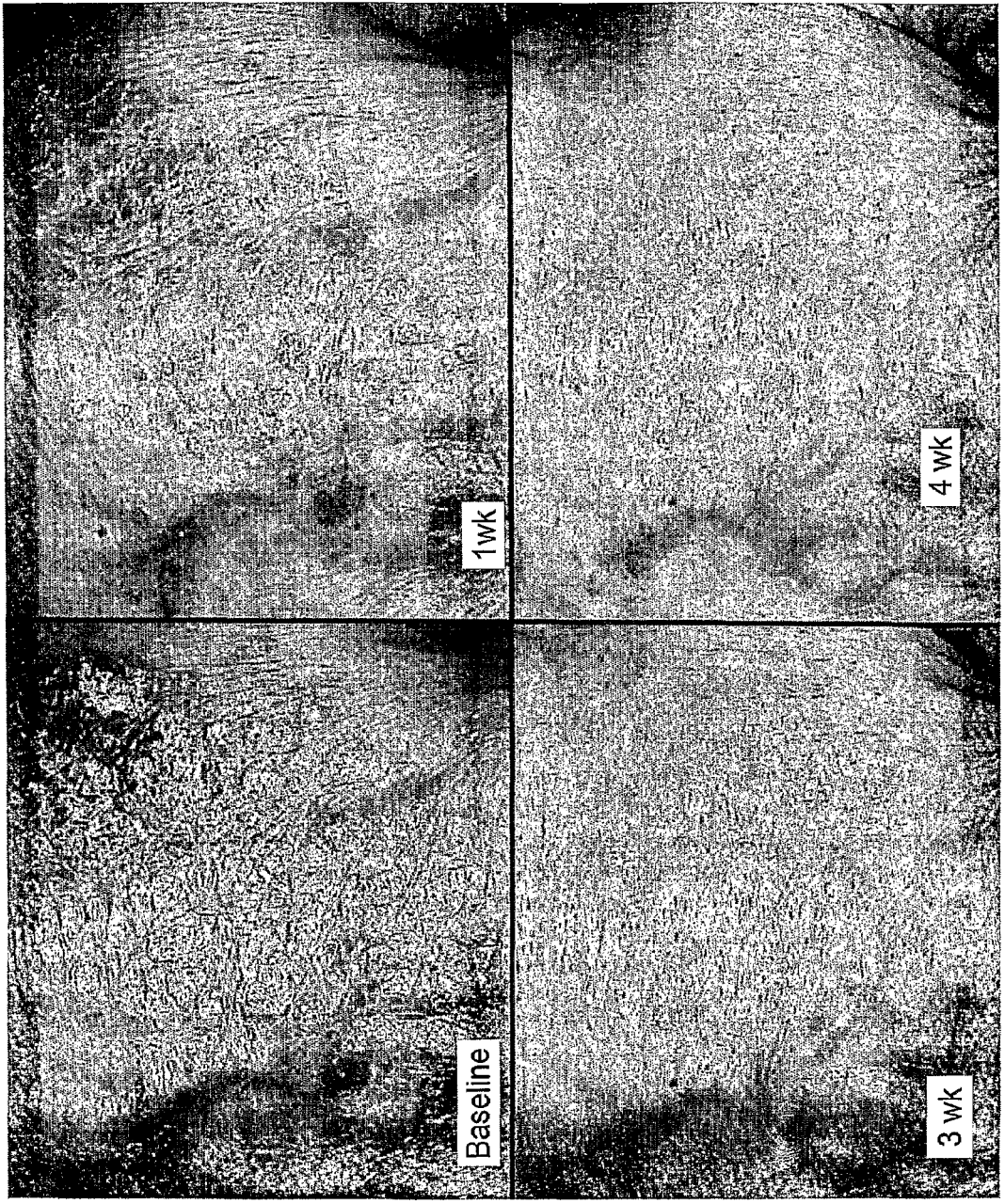

METHOD OF TREATING SKIN DISEASES

The present invention relates to a method for the topical treatment of a variety of skin diseases and skin problems.

The treatment of the present invention consists of the topical administration of an acetylcholinesterase inhibitor such as galantamine hydrobromide or donepezil hydrochloride. It should be noted that the compound here referred to as "galantamine" was previously known as "galanthamine". These agents inhibit the hydrolysis of the transmitter acetylcholine which is located in the interstitial fluid or presynaptic cleft. It is postulated that the hydrolysis of acetylcholine is augmented in oedema and various inflammatory states of the skin. Also it has been shown that the nicotinic receptor is involved in the control of calcium influx into cells and different immune reactions involved in inflammation and trauma.

It has been shown (cf. "A nicotinic acetylcholine receptor regulating cell adhesion and motility is expressed in human keratinocytes" Grando S A et al. J. Invest. Dermatol, 105:6.6 1995 December, 774-81) that keratinocytes have nicotinic and muscarinic receptors that have an important role in the normal life cycle of the skin.

Acetylcholine is a classical neurotransmitter that has increasingly been recognized to occur in a large variety of cells outside the central nervous system (CNS). Acetylcholine has been shown to be produced in fibroblasts, melanocytes, endothelial cells and cells of the immune system. Acetylcholine can alter a variety of cellular functions where it acts on cells through its two classes of receptors, nicotinic acetylcholine receptors and muscarinic receptors. The nicotinic acetylcholine receptor is a ligand-gated ion channel formed by five subunits: alpha 3, alpha 5, beta 2 and beta 4 subunits, and by alpha 7 subunits that can form functional nicotinic receptors of their own. The presence of these structures, i.e. in keratocytes, can be shown by histochemical methods, i.e. antibodies to alpha 3 or alpha 7 subunits.

The importance of acetylcholine in inflammation can also be determined by measuring the augmentation of the activity of the hydrolysing enzyme of acetylcholine, acetylcholinesterase, for instance in rheumatoid arthritis in the synovial fluid (cf. Snorrason, Ernir: U.S. Pat. No. 6,358,941 B1. See also U.S. Pat. No. 5,312,817. Snorrason, Ernir, May 14, c.f. the importance of treating oedema of the CNS with these agents.). In this context it should be noted that acetylcholinesterases inhibitors augment cortisol and endorphin release. (cf Cozantis D. A. Galanthamine hydrobromide versus neostigmine: a plasma cortisol study in man, Anaesthesia 1974;29:163-168.). Galantamine augments cortisol releasing hormone (CRH) by augmenting the cholinergic input to the hypothalamus. It has also been shown that galantamine augments endorphin release (c.f. Cozantis, op. cit.). Recently it has been demonstrated that the nicotinic acetylcholine receptor α7 subunit is found on the surface of macrophages and that stimulation of this receptor leads to inhibition of the release of tumour necrosis factor (TNF) from macrophages and thus could control various inflammatory states of the skin (Wang, H., M. Yu, M. Ochani, C. A. Amelia, M. Tanovic, S. Susarla, J. H. Li, H. Wang, H. Yang, L. Ulloa, Y. Al-Abed, C. J. Czura, and K. J. Tracey. "Nicotinic Acetylcholine Receptor Alpha7 Subunit Is an Essential Regulator of Inflammation." Nature 421, no. 6921 (2003): 384-8.)

I have now surprisingly found that skin problems can be treated locally by the topical application of one or more acetylcholinesterase inhibitors and that the main action in pathological states of the skin is local to keratocytes and other skin cells. This can be shown by administering topical agents containing acetylcholinesterase inhibitors (e.g. creams) directly to the skin lesions.

Thus, the present invention consists in a method of treating skin diseases or problems of a mammal, which may be human, by the topical administration to the site of the disease or problem of an acetylcholinesterase inhibitor.

The invention also provides the use of an acetylcholinesterase inhibitor for the manufacture of a medicament for the topical treatment of skin diseases and skin problems.

It should be noted that all of the indications to which the present invention applies are non-arthritic.

Although the primary use of the compounds of the present invention is expected to be for the treatment or prevention of skin diseases in humans, they may also be used to treat other animals, especially, but not exclusively, mammals, and so they may have application in veterinary medicine.

The accompanying drawing shows the progress of psoriasis on the hand of a 62 year old female patient over a 4 week period, as described hereafter in Example 2.

The skin diseases and problems to which the present invention is applicable include:

A. Papulosquamous and Eczematous Dermatoses. Psoriasis, pityriasis rosea, pityriasis rubra pilaris, pityriasis lichenoides et varioliformis acuta and chronica, parapsoriasis group of disorders, erythoderma, lichen planus and lichenoid disorders, atopic dermatitis, allergic contact dermatitis, irritant contact dermatitis, other eczematous disorders such as seborrhoeic dermatitis and other eczematous disorders.

B. Vesiculobullous Diseases: Pemphigus, pemphigoid, dermatitis herpetiformis, epidermalysis bullosa, linear IgA dermatosis and other bullous disorders C. Adnexal Diseases: Acne vulgaris, acne rosacea (rosacea), perioral dermatitis, folliculitis, hyperhidrosis, Grover's disease, D. Rheumatologic disorders (skin symptoms): Different forms of lupus erythematous, dermatomyosistis, systemic sclerosis, other rheumatologic disorder such as Sjogren's syndrome, mixed connective tissue disease and cutaneous manifestations of rheumatologic disorders, morphea, lichen sclerosus and atrophicus, panniculitis, E. Disorders due to physical agents: Disorders caused by radiation, including UV light and sunburn, photodamage, disorders caused by abnormal reaction to UV light such as polymorphous light eruption, burns and diseases caused by heat or cold, chemical burns, frictional and traumatic injuries to the skin. Disorders and states caused by normal or abnormal aging of the skin including wrinkles. Ulcers of the skin, caused by impaired blood flow, infections, pressure, vasculitis or immunological mechanisms.

F. Urticria eythema and purpura: Urticaria and angioedema, erythema multiforme, erythema annuare centrifugum and other erythmatous disorders, drug reactions of the skin, vasculitis and purpura of the skin, neutrophilic dermatoses and pregnancy dermatoses.

G. Prevention or treatment of neoplastic disorders of the skin: Malignant melanoma, squamous cell carcinoma, basal cell carcinoma, pre-malignant disorders, benign skin tumours, actinic keratoses and premalignant conditions.

H. Other disorders, signs or symptoms of the skin: Pruritus, neuralgia, abnormal sensation or pain states, such has burning, oedema of the skin. Alopecia areata, alopecia androgenica, hypopigmentation including vitiligo, hyperpigmentation.

The acetylcholinesterase inhibitor is preferably formulated with conventional diluents and excipients such as are well known for use in topical formulations. The active compound is preferably formulated as a gel, cream, spray, lotion or ointment.

Although galantamine is only an example of an acetylcholinesterase inhibitor for use in the present invention, other acetylcholinesterase inhibitors may equally be used. Examples of such compounds include galantamine derivatives, such as those compounds of formula (I):

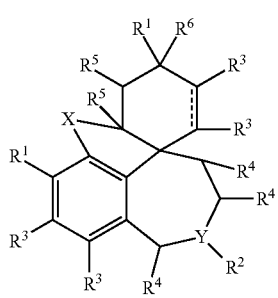

(I)

in which:
the dotted line indicates that there is a single or double carbon-carbon bond;

the two symbols $R^1$ are the same as or different from each other and each represents a hydrogen atom, a hydroxy group, an alkyl group, an aryl group, an aralkyl group, a hydroxyalkyl group, a thioalkyl group, a carboxyalkyl group, a carboxyalkylamino group, an alkylamino group, an acyl group, a cyano group, a sulphhydryl group, a $C_1$-$C_6$ alkoxy group, an alkylthio group, an aryloxy group, an arylthio group, an aliphatic or aromatic carbamoyl group, an aralkoxy group, an aralkylthio group, an aryloxymethyl group, an alkanoyloxy group, a hydroxyalkanoyloxy group, a benzoyloxy group, a benzoyloxy group substituted by one or more groups $R^3$, as defined below, or an aryloxycarbonyl group;

$R^2$ represents a hydrogen atom, a $C_1$-$C_6$ alkyl group, a $C_2$-$C_6$ alkenyl group (e.g. an allyl group), an aralkyl group, said alkyl, alkenyl and aralkyl groups being unsubstituted or being substituted by at least one halogen atom, a cycloalkyl group, a hydroxy group, an alkoxy group, a nitro group, an amino group, an aminoalkyl group, an acylamino group, an aromatic or non-aromatic heterocyclic group (e.g. an α- or β- furyl group, an α- or β- thienyl group, an α- or β- thenyl group, a pyridyl group, a pyrazinyl group, or a pyrimidyl group), an alkyl group substituted by an aromatic heterocyclic group, an aryl group (e.g. a phenyl group), an aralkyl group, a cyano group, an aroyl group, or a cycloalkylmethyl group;

the symbols $R^3$ are the same as or different from each other and each represents a hydrogen atom, a hydroxy group, an alkyl group, an aryl group, an aralkyl group, a hydroxyalkyl group, a thioalkyl group, a sulphhydryl group, a $C_1$-$C_6$ alkoxy group, an aryloxy group, an arylthio group, an aralkoxy group, an aralkylthio group, a nitro group, an amino group, an alkylamino group, an acylamino group, an aralkylamino group, a halogen atom or a trifluoromethyl group;

the symbols $R^4$ are the same as or different from each other and each represents a hydrogen atom, a halogen atom, a trifluoromethyl group, or a $C_1$-$C_4$ alkyl group;

the two symbols $R^5$ are the same as or different from each other and each represents a hydrogen atom, or a hydroxymethyl group;

$R^6$ represents a hydrogen atom or a $C_1$-$C_6$ alkyl group, or, when the symbol $R^1$ attached to the same carbon atom as $R^6$ represents a hydrogen atom, $R^6$ represents a group of formula (Ia):

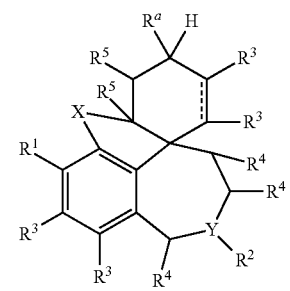

(Ia)

where Ra represents a linking bond, and $R^1$, $R^2$, $R^3$, $R^4$, $R^5$, X and Y are as defined for formula (I);

or $R^6$ and the symbol $R^1$ attached to the same carbon atom as $R^6$ together represent a semicarbazone;

X represents an oxygen atom or a group of formula —$NR^3$, where $R^3$ is as defined above;

Y represents a nitrogen atom or a phosphorus atom;

and pharmaceutically acceptable salts thereof.

In the compounds of formula (I) above, except where otherwise indicated, alkyl groups may be straight or branched chain and preferably have from 1 to 10 carbon atoms, and examples of these include the methyl, ethyl, propyl, isopropyl, butyl, isobutyl, sec-butyl, t-butyl, pentyl, hexyl, heptyl, octyl, nonyl and decyl groups. Alkoxy groups and other simple derivatives of the alkyl groups likewise preferably have from 1 to 10, more preferably from 1 to 6, carbon atoms.

Aryl and heterocyclic groups may be unsubstituted or they may be substituted by one or more substituents selected from the groups and atoms defined for $R^3$, provided that any $R^3$ substituent may not itself be further substituted by a substituted aryl or heterocyclic group.

Preferred halogen atoms are the fluorine, chlorine, bromine and iodine atoms.

Preferred compounds of formula (I) are those in which the alkyl groups contain from 1 to 8, more preferably from 1 to 6, carbon atoms, halogen atoms are fluorine, chlorine or bromine atoms, aryl groups are the phenyl group (which may be substituted or unsubstituted, preferably unsubstituted), cycloalkyl groups contain from 3 to 7 ring carbon atoms (preferably cyclopropyl or cyclobutyl), acyl groups are lower (e.g. $C_2$-$C_6$ alkanoyl groups) and heterocyclic groups are aromatic and contain from 5 to 8 ring atoms (e.g. the thienyl, furyl, pyridyl, pyrrolyl or pyrazinyl groups).

Particularly preferred compounds for use in the present invention are those compounds of formula (II):

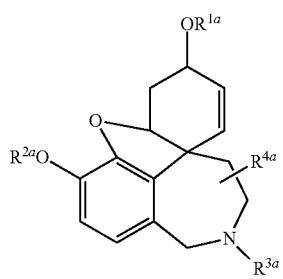

(II)

where:
$R^{1a}$ and $R^{2a}$ are the same as or different from each other and each represents a hydrogen atom, an acyl group (preferably a lower alkanoyl group, such as an acetyl group) or a $C_1$-$C_6$ alkyl group (such as a methyl, ethyl, propyl or isopropyl group);
$R^{3a}$ represents an alkyl, alkenyl or aralkyl group, any of which may be unsubstituted or substituted by one or more halogen atoms, or it represents a cycloalkyl, hydroxy, alkoxy, nitro, amino, aminoalkyl, acylamino, aromatic heterocyclic, aroyl, aroylalkyl or cyano group; and
$R^{4a}$ represents a hydrogen or halogen atom;
and pharmaceutically acceptable salts thereof, especially the hydrobromide, hydrochloride, methylsulphonate or methiodide.

Of these compounds, we particularly prefer galantamine and its salts or donepezil and its salts, especially the halides, such as galantamine hydrobromide or donepezil hydrochloride.

Galantamine derivatives which may be used in the present invention include norgalantamine, norgalantamine derivatives and epigalantamine.

Other compounds which may be used as the acetylcholinesterase inhibitor include: physostigmine, tacrine and tacrine analogues, fasciculin, metrifonate, heptyl-physostigmine, norpyridostigmine, norneostigmine, neostigmine, pyridostigmine, huperzine or a prodrug therefor, rivastigmine or a prodrug therefor, gossypol or phenserine, or a prodrug therefor.

Another particularly preferred acetylcholinesterase inhibitor is donepezil and its salts, especially the halides, such as donepezil hydrochloride.

The compounds of the present invention are applied topically to the site of the skin trauma, disease or disorder or other problem. To facilitate this, they are preferably formulated in a suitable form for topical administration, especially gel, cream, spray, lotion or ointment. Thus, the formulations used in the present invention comprise the active compound, the acetylcholinesterase inhibitor, in admixture with one or more acceptable carriers and optionally other therapeutic ingredients. The carrier(s) must be acceptable in the sense that they should be compatible with the other ingredients of the formulation and not deleterious to the patient.

There is no particular restriction on the content of the acetylcholinesterase inhibitor in the formulation, the amount depending on the dose of the active compound which it is desired should be applied. However, a formulation administered to the site of a lesion and containing the acetylcholinesterase inhibitors of the present invention has a minimal systemic effect because of the low blood concentration when these agents are applied topically. A concentration of the active ingredient ranging from 0.05 to 2% by weight is usually preferred, an amount from 0.005 to 1% of the total weight of the topical formulation being most preferred.

The topical agent is preferably water-based. It may contain other conventional additives, for example emulsifying agents such as hydroxymethyl cellulose, hydroxypropylmethyl cellulose, and stabilisers such as polyvinylpyrrolidone.

Other conventional additives may be included, as is well known to those skilled in the art.

The acetylcholinesterase inhibitor may also be applied to a wound, lesion, trauma or other skin disorder on a wound dressing, such as a plaster, band-aid or the like.

CLINICAL TESTS

Clinical testing with ointments containing acetylcholinesterase inhibitors has been started in the following clinical entities: psoriasis, inflammation because of trauma, atopic dermatitis, wound healing, sun burn and wrinkles The basic assumption is that topical agents containing acetylcholinesterase inhibitors influence the normal cycle of the renewal of the skin and improve this process in pathological states. Also it is thought to decrease local oedema by favouring the influx of calcium from the interstitial fluid, thereby restoring the normal fluid balance in local lesions of various kinds where oedema is one of the symptoms. It is also possible that the nicotinic acetylcholine receptor found on the surface of macrophages leads to inhibition of the release of tumour necrosis factor (TNF) from macrophages and thus could control various inflammatory states of the skin. It has also been observed that pain and pruritus decrease.

The prototype medication used here as cholinesterase inhibitors are galantamine hydrobromide and donepezil hydrochloride (also called E2020, empirical formula $C_{24}H_{29}NO.3HCl$, also called Aricept).

EXAMPLE 1

The gel used was of the following composition:

| | |
|---|---|
| HPMC (hydroxypropyl methyl cellulose) | 3% |
| PVP-40 (polyvinylpyrrolidone) | 1% |
| Donepezil HCl or Galantamine HBr | 0.1 or 1.0% |
| $H_2O$ | balance |

Patients for the treatment of psoriasis(five patients) were chosen as having a relatively secure diagnosis of plaque type psoriasis vulgaris with silvery scales covering the surface of the lesion. This disease tends to be chronic, and often difficult to treat with topical agents. All of the five patients treated were diagnosed by a dermatologist and had the diagnosis for over three years. None of these patients had arthritis.

Psoriasis is a hyper proliferative disease with altered differentiation of the keratinocytes. The keratinocytes in psoriatic skin lesions have an increase in the rate of maturation and it takes 3 to 4 days for a psoriatic basal cell to reach the horny layer, compared with the normal 3-4 weeks.

After a treatment, which may vary from two weeks to one month, there was a considerable improvement both scaling, size, thickness and erythematous appearance of the lesions. The lesions in these patients were all symmetric and each patient was treated with the formulation of the present invention without the active compound on one side and with the active compound on the other. Each patient was treated as his own control (simple blind).

In one patient, a lesion which had been present for three years almost disappeared after treatment for one month. Pruritus had been present in all the patients but with varying severity. All of the patients reported an absence of itching during the treatment.

The treatment consisted of applying a gel containing 0.1% of the active compound for two days twice daily and then switching to the ointment containing 1% of the active compound as no adverse effect was noticed. Two patients were treated with galantamine and three patients with donepezil.

Similar trials were carried out in wrinkles, where 12 women between fifty and sixty years of age were treated once a day three times a week for eight weeks. All patients reported improvement in skin texture and reduction of fine lines and this view was shared by their dermatologist. The women reported that the results achieved were comparable with or better than more expensive skin treatments of various sorts.

In wound healing, two patients who had chronic ulcers or wounds that did not heal became considerably better after treatment for four weeks.

The treatment was also carried out in a group of people with severe sunburn where it controlled pain, erythema and itching.

There are indications that this kind of treatment lessens oedema produced by trauma, and is especially fast in the acute phase of the inflammation.

EXAMPLE 2

The patient was a 62 year old woman with plaque psoriasis, who showed a dramatic regression of skin lesions following therapy with 0.5% topical donepezil hydrochloride cream (TDH).

The clinical diagnosis of psoriasis had been made at the age of 58. At that time, the patient had typical psoriasis plaques at the knees and elbows. She had previously been treated with topical agents, both corticosteroids and salicylic acid. This treatment gave partial remission of psoriatic lesions, but complete remission was never achieved. As the patient did not want to take oral medications and because she was no longer responsive to topical therapy, the patient elected to continue only with moisturizers. Thus, prior to the current treatment with TDH the patient had only used moisturizers for the last three years. During this time her lesions were stable.

The patient's progress over a 4 week period is shown in the accompanying drawing. The first part of this drawing shows the hand of the patient at presentation before starting treatment with TDH. At this time, the patient had thick psoriasis plaques at the dorsal area of the hands, elbows and knees and lesions in intertigenous areas. The lesions were slightly itchy and, except in the intertrigenous areas, they were covered with silvery scales.

The patient started treatment with 0.5% THD cream b.i.d. The patient noted after 2 days of therapy that the itching stopped. After seven days (drawing part 2), the scales had disappeared, infiltration could still be detected, but lesions were considerably thinner. After three weeks (thawing part 3), the lesions had almost disappeared, infiltration could not be detected, but some residual erythema could still be seen. After four weeks of treatment (drawing part 4), all lesions had completely disappeared. The patient continued treatment for a further two weeks after the symptoms had disappeared. At four weeks after stopping treatment, there was still no sign of reappearance of the psoriasis lesions. The treatment was well tolerated with no local or systemic side effects.

The pathogenesis of psoriasis is still not completely understood. For many years psoriasis was considered to be mainly an epidermal disease, but various systemic abnormalities have been demonstrated in relation to inflammation and immune function. The T-lymphocyte is the predominant cell in the psoriatic infiltrate and ciclosporin and the newer biologic therapies all have an effect on the T-cell response and have been shown to be effective in the treatment of psoriasis.

There is evidence that the extraneuronal cholinergic system is involved in regulating several functions of the skin independent of neuronal innervation. It has been shown that keratinocytes and melanocytes synthesize acetylcholine. Acetylcholine acts via two major signals, the nicotinic and muscarinic receptors. The cholinergic system has been thought to be involved in the apoptosis that occurs when keratinocytes differentiate from stratum granulosum to stratum corenum. Furthermore the extraneuronal cholinergic system is involved in microcirculation, terminal differentiation of the skin, sweat and sebum secretion and barrier formation.

It has been shown that keratinocytes have nicotinic and muscarinic receptors that have an important role in the normal life cycle of the skin. Additionally it has been demonstrated that keratinocyte adhesion is controlled by acetylcholine. Also it has been demonstrated that acetylcholine in vitro stimulates keratinocyte growth and spreading, and is thus likely to promote re-epithelization of the skin in wound healing.

The muscarinic receptors on skin fibroblasts, keratinocytes and melanocytes have five subtypes and lead either to inhibition of cAMP or regulate intracellular calcium levels. The exact role of these receptors still remains to be elucidated, but they have been implemented in control of melanogenesis amongst other functions. The nicotinic receptors have a different molecular construction and even these receptors have several molecular subtypes. The nicotinic receptors form ion channels that gate either sodium, potassium or calcium. It has been postulated that the nicotinic receptor plays a central role in terminal differentiation and barrier formation of the epidermis.

The importance of acetylcholine in inflammatory states has been demonstrated by increased activity of the hydrolysing enzyme of acetylcholine, acetylcholinesterase, in the synovial fluid of patients with rheumatoid arthritis.

Thus it has been demonstrated that acetylcholine is an important molecule that controls several important functions of the skin. It is possible that inflammation in the psoriasis lesions, similarly as has been described in patients with rheumatoid arthritis, leads to decreased amounts of acetylcholine in the skin and thus decreased keratinocyte adhesion and loss of control of keratinocyte differentiation. By applying TDH to the skin normal levels of acetylcholine are restored and keratinocyte homeostasis is brought back to normal, and thus reversing the pathology in the psoriasis lesions. It has recently been demonstrated that tumour necrosis factor plays an important role in both plaque psoriasis and psoriatic arthritis and that drugs that inhibit TNF can control both the skin and arthritic symptoms. It is therefore possible that, via the nicotinic acetylcholine receptor found on the surface of macrophages, there is inhibition of the release of tumour necrosis factor (TNF) from macrophages and this could control the inflammatory state in the psoriasis lesions.

Donepezil hydrochloride has been shown to be a safe molecule in several studies on Alzheimer's disease where the drug is used orally. It is likely that site effects are even less when used topically. In the patients described above no site effects were seen. We therefore believe that the cholinergic system in the skin is a novel pharmacological target and that topical acetylcholine inhibitors might become important topical drugs in the treatment of skin diseases. We believe this case demonstrates that the extraneural cholinergic system might be involved in the pathogenesis of psoriasis and that it merits further research on the extraneural cholinergic system in health and diseases states of the skin.

The invention claimed is:

1. A method of treating plaque psoriasis (psoriasis vulgaris) in a mammal in need thereof, the method comprising topically administering to a psoriasis plaque on the mammal a formulation comprising donepezil hydrochloride, wherein (1) the formulation is in a form selected from the group consisting of a gel, a cream, and an ointment; and (2) the concentration of donepezil hydrochloride is 0.05% to 2% by weight of the formulation.

2. The method of claim 1, wherein the formulation is topically administered to the psoriasis plaque twice daily for a duration of two to six weeks.

3. The method of claim 1, wherein the concentration of donepezil hydrochloride is 0.1% by weight of the formulation.

4. The method of claim 1, wherein the concentration of donepezil hydrochloride is 0.5% by weight of the formulation.

5. The method of claim 1, wherein the concentration of donepezil hydrochloride is 1.0% by weight of the formulation.

6. The method of claim 1, wherein the formulation is in the form of the gel.

7. The method of claim 6, wherein the gel comprises hydroxypropyl methylcellulose (hypromellose), polyvinylpyrrolidone (povidone), and water.

8. The method of claim 1, wherein the formulation is in the form of the cream.

9. The method of claim 1, wherein the mammal is a human.

10. The method of claim 3, wherein the mammal is a human.

11. The method of claim 4, wherein the mammal is a human.

12. The method of claim 5, wherein the mammal is a human.

* * * * *